United States Patent [19]
Todd et al.

[11] Patent Number: 6,140,055
[45] Date of Patent: Oct. 31, 2000

[54] ZYMOGENIC NUCLEIC ACID DETECTION METHODS AND RELATED KITS

[75] Inventors: Alison V. Todd, Glebe; Caroline J. Fuery, Sydney; Murray J. Cairns, Woy Woy, all of Australia

[73] Assignee: Johnson & Johnson Research Pty Limited, Australia

[21] Appl. No.: 09/253,955

[22] Filed: Feb. 22, 1999

Related U.S. Application Data

[60] Provisional application No. 60/076,899, Mar. 5, 1998.

[51] Int. Cl.[7] .............................. C12Q 1/68; C12P 19/34; C07H 21/04
[52] U.S. Cl. ........................ 435/6; 435/91.2; 536/23.2; 536/24.33
[58] Field of Search .................. 435/6, 91.2, 810; 536/23.2, 24.33

[56] References Cited

U.S. PATENT DOCUMENTS

| | | | |
|---|---|---|---|
| 4,000,159 | 12/1976 | Scoggins et al. | 260/326.5 |
| 4,683,195 | 7/1987 | Mullis et al. | 435/91.2 |
| 4,683,202 | 7/1987 | Mullis | 435/6 |
| 4,965,188 | 10/1990 | Mullis et al. | 435/6 |
| 5,112,734 | 5/1992 | Kramer et al. | 435/6 |
| 5,176,995 | 1/1993 | Sninsky et al. | 435/6 |
| 5,436,143 | 7/1995 | Hyman | 435/91.2 |
| 5,582,988 | 12/1996 | Backus et al. | 435/6 |
| 5,602,000 | 2/1997 | Hyman | 435/91.1 |
| 5,874,414 | 2/1999 | Haseloff et al. | 514/44 |
| 5,955,653 | 9/1999 | Scott et al. | 800/303 |

FOREIGN PATENT DOCUMENTS

| | | |
|---|---|---|
| WO94/29481 | 12/1994 | WIPO. |
| WO/96/27026 | 9/1996 | WIPO. |
| WO96/32500 | 10/1996 | WIPO. |
| WO96/17087 | 6/1997 | WIPO. |

OTHER PUBLICATIONS

F.F. Chehab, et al. (1987) *Nature* 329:293–294.

R.K. Saiki, et al. (1985) *Science* 230:1350–1354.

Walker, G.T., et al. (1992) Strand Displacement Amplification—an isothermal, in vitro DNA amplification technique. *Nucleic Acids Res.* 20:1691.

Jonas, V., et al. (1993) Detection and identification of Mycobacterium tuberculosis directly from sputum sediments by amplification of rRNA. *Journal of Clinical Microbiology* 31:2410–2416.

Fahy, E., et al. (1991) Self–sustained sequence replication (3SR) : An iso–thermal transcription–based amplification alternative to PCR. *PCR Methods Appl* 1: 25–33.

Nazarenko, I.A., et al. (1997) A closed tube format for amplification and detection of DNA based on energy transfer. *Nucleic Acids Research* 25: 2516–2521.

Tyagi, S. and Kramer, F.R. (1996) Molecular Beacons: Probes that fluoresce on hybridization. Nature Biotechnology 14: 303–308.

Lee, L.G., Connell, C.R. and Bloch, W. (1993) Allelic discrimination by nick–translation PCR with fluorogenic probes. *Nucleic Acids Research* 21:3761–3766.

(List continued on next page.)

*Primary Examiner*—Kenneth R. Horlick
*Attorney, Agent, or Firm*—Alan J. Morrison

[57] ABSTRACT

This application provides methods of detecting and quantitatively determining a target nucleic acid sequence in a sample, which comprise contacting the sample with a primer and a zymogene which encodes, but which itself is the anti-sense sequence of, a catalytic nucleic acid sequence, so that when the target is present, a single amplified nucleic acid molecule is produced which comprises the sequences of both the target and catalytic molecules. This invention further provides a method of simultaneously detecting the presence of a plurality of target nucleic acid sequences in a sample. Finally, this invention provides molecules and kits for practicing the instant methods.

24 Claims, 1 Drawing Sheet

Homogeneous PCR amplification and detection

OTHER PUBLICATIONS

Urdea, M. (1993) Synthesis and characterization of branched DNA (bDNA) for direct and quantitative detection of CMV, HBV, HCV, and HIV. *Clin. Chem.* 39: 725–726.

Eigen, M. and Rigler, R. (1994) Sorting single molecules: Application to diagnostics and evolutionary biotechnology. *PNAS* 91:5740–5747.

Perriman, R. and Gerlach, W.L. (1992) Extended target site specificity for a hammered ribozyme. *Gene* 113:157–163.

Breaker, R.R. and Joyce, G. (1994) A DNA enzyme that cleaves RNA. *Chemistry and Biology* 1:223–229.

Koizumi, M., et al. (1989) Design of RNA enzymes distinguishing a single base mutation in RNA. *Nucleic Acids Research* 17:7059–7069.

E. Otsuka and M. Koizumi, Japanese Patent No. 4,235,919.

Kashani–Sabet, M., et al. (1992) Reversal of the malignant phenotype by an anti–ras ribozyme. *Antisense Research and Development* 2:3–15.

Raillard, S.A. and Joyce, G.F. (1996) Targeting sites within HIV–1 cDNA with a DNA cleaving ribozyme. *Biochemistry* 35:11693–11701.

Carmi, N., et al. (1996) In vitro selection of self–cleaving DNAs. *Chemistry and Biology* 3:1039–1046.

Komatsu, Y., Koizumi, M., Sekiguchi, A. and Ohtsuka, E. (1993) Cross–ligation and exchange reactions catalyzed by hairpin ribozymes. *Nucleic Acid Research* 21:185–190.

Santoro, S.W. and Joyce, G. (1997) A general purpose RNA–cleaving DNA enzyme. *PNAS* 94:4262–4266.

Cuenoud, B. and Szostak, J.W. (1995) A DNA metalloenzyme with DNA ligase activity. *Nature* 375:611–614.

Li, Y. and Sen, D.A. (1996) A catalytic DNA for porphorin metallation. *Nature Struct. Biol.* 3:734–747.

Tarasow, T.M., Tarasow, S.L. and Eaton, B.E. (1997) RNA–catalyzed carbon–carbon bond formation. *Nature* 389: 54–57.

Illangasekare, M., Sanchez, Nickles, T., and Yarus, M. Aminoacyl–RNA synthesis catalyzed by an RNA. *Science* 267:643–647.

Lohse, P.A. and Szostak, J.W. (1996) Ribozyme–catalyzed amino–acid transfer reactions. *Nature* 381: 442–444.

Breaker, R.R. DNA enzymes (1997) *Nature Biotechnology* 15: 427431.

*Promega Protocols and Applications Guide.* Titus, D.E. (Ed) Promega Corporation (1991).

Kramvis, A., Bukofzer, S. and Kew (1996) Comparison of Hepatitis B virus DNA extractions from serum by the QIAamp blood kit, Genereleaser, and the Phenol–chloroform method. *Journal of Clinical Microbiology* 34: 2731–2733.

Yong, S.L., Thomas, R.J.S. and Phillips, W.A. (1995) Single–step direct PCR amplification from solid tissues. *Nucleic Acids Research* 23:1640.

Sambrook, J., Fritsch, E.F. and Maniatis, T. (1989) *Molecular Cloning: A Laboratory Manual.* 2nd Ed., New York: Cold Spring Harbour Laboratory Press.

0PCR Systems, Reagents and Consumables. Perkin Elmer Catalogue 1996–1997. Roche Molecular Systems, Inc., Branchburg, New Jersey, USA.

Walder, R.Y., Hayes, J.R. and Walder J.A. (1993) Use of PCR primers containing a 3'–terminal ribose residue to prevent cross–contamination of amplified sequences. Nucleic Acid Research 21(18):4339–4343.

Homogeneous PCR amplification and detection

ZYMOGENIC NUCLEIC ACID DETECTION METHODS AND RELATED KITS

This application claims the benefit of U.S. provisional application No. 60/076,899, filed Mar. 5, 1998.

Throughout this application, various publications are cited. The disclosure of these publications is hereby incorporated by reference into this application to describe more fully the state of the art to which this invention pertains.

FIELD OF THE INVENTION

This invention relates to methods of detecting and quantitating target nucleic acid molecules in a sample via nucleic acid amplification. In the instant methods, a single amplicon is produced containing both catalytic nucleic acid and target sequences. The catalytic nucleic acid is synthesized from its anti-sense, zymogenic precursor only if the target is present.

BACKGROUND OF THE INVENTION

Methods of in vitro nucleic acid amplification have widespread applications in genetics, disease diagnosis and forensics. In the last decade many techniques for amplification of known nucleic acid sequences ("targets") have been described. These include the polymerase chain reaction ("PCR") (1–7, 41), the strand displacement amplification assay ("SDA") (8) and transcription-mediated amplification ("TMA") (9, 10) (also known as self-sustained sequence replication ("SSR")). The amplification products ("amplicons") produced by PCR and SDA are DNA, whereas RNA amplicons are produced by TMA. The DNA or RNA amplicons generated by these methods can be used as markers of nucleic acid sequences associated with specific disorders.

Several methods allow simultaneous amplification and detection of nucleic acids in a closed system, i.e., in a single homogeneous reaction system. These methods include Sunrise™ primers (11), Molecular Beacons (12) and the Taqman™ system (13). Using homogeneous sealed tube formats has several advantages over separately analyzing amplicons following amplification reactions. Closed system methods are faster and simpler because they require fewer manipulations. A closed system eliminates the potential for false positives associated with contamination by amplicons from other reactions. Homogeneous reactions can be monitored in real time, with the signal at time zero allowing the measurement of the background signal in the system. Additional control reactions for estimating the background signal are therefore not required. A change in the signal intensity indicates amplification of a specific nucleic acid sequence present in the sample.

Instead of amplifying the target nucleic acid, alternate strategies involve amplifying the reporter signal. The Branched DNA assay (14) amplifies the signal by employing a secondary reporter molecule (e.g. alkaline phosphatase), whereas fluorescence correlation spectroscopy (FCS) employs electronic amplification of the signal (15).

As with other amplification technologies, catalytic nucleic acids have been studied intensively in recent years. The potential for suppression of gene function using catalytic nucleic acids as therapeutic agents is widely discussed in the literature (16–22). Catalytic RNA molecules ("ribozymes") have been shown to catalyze the formation and cleavage of phosphodiester bonds (16, 23). In vitro evolution techniques have been used to discover additional nucleic acids which are capable of catalyzing a far broader range of reactions including cleavage (21, 22, 24) and ligation of nucleic acids (25), porphyrin metallation (26), and formation of carbon-carbon (27), ester (28) and amide bonds (29).

Ribozymes have been shown to be capable of cleaving both RNA (16) and DNA (21) molecules. Similarly, catalytic DNA molecules ("DNAzymes") have also been shown to be capable of cleaving both RNA (17, 24) and DNA (22, 30) molecules. Catalytic nucleic acid can cleave a target nucleic acid substrate provided the substrate meets stringent sequence requirements. The target substrate must be complementary to the hybridizing regions of the catalytic nucleic acid and contain a specific sequence at the site of cleavage. Examples of sequence requirements at the cleavage site include the requirement for a purine:pyrimidine sequence for a class of DNAzymes ("10-23 model" or "10-23 DNAzyme") (24), and the requirement for the sequence U:X where X can equal A, C or U but not G, for hammerhead ribozymes (16).

In addition to having therapeutic potential, catalytic nucleic acid molecules can also be used as molecular tools in genetic diagnostic assays. For example, ribozymes have been used to facilitate signal amplification in a two-stage method (31–33). In the first stage, a test sample is contacted with inactive oligonucleotides. This contacting results in the production of "triggering" RNA oligonucleotides when the sample contains the target sequence. In the second stage the triggering RNA oligonucleotides induce an amplification cascade. This cascade results in the production of large quantities of catalytically active reporter ribozymes which, when detected, indicate the presence of the target sequence in the test sample. The target sequence itself is not amplified during the process. Rather, only the reporter signal is amplified.

In short, target nucleic acid amplification and reaction conditions permitting same are known. Catalytic nucleic acid molecules, and reaction conditions permitting their activity are also known.

However, no method has ever existed which permits the simultaneous processes of nucleic acid amplification and catalytic nucleic activity in a single reaction milieu. Moreover, no target amplification method has ever been performed wherein the amplification product is a single nucleic acid molecule containing sequences for the target and the catalytic nucleic acid molecule. Finally, no target amplification method has ever employed an anti-sense, zymogenic sequence of a catalytic nucleic acid molecule which, only in the presence of target sequence, is amplified in its "sense", catalytic form.

SUMMARY OF THE INVENTION

This invention provides a method of detecting the presence of a target nucleic acid sequence in a sample which comprises (a) contacting the sample, under conditions permitting primer-initiated nucleic acid amplification and catalytic nucleic acid activity, with
  (i) a DNA primer suitable for initiating amplification of the target, and
  (ii) a DNA zymogene which encodes, but which itself is the anti-sense sequence of, a catalytic nucleic acid molecule, wherein the primer and zymogene are situated with respect to each other so that, when the target is present, a single amplified nucleic acid molecule is produced which comprises the sequences of both the target and catalytic nucleic acid molecule; and (b) determining the presence of catalytic nucleic acid activity, thereby determining the presence of the target nucleic acid sequence in the sample.

This invention also provides a method of simultaneously detecting the presence of a plurality of target nucleic acid sequences in a sample which comprises
(a) contacting the sample, under conditions permitting primer-initiated nucleic acid amplification and catalytic nucleic acid activity, with
  (i) a plurality of primers wherein for each target being detected, there exists at least one primer suitable for initiating amplification of that target, and
  (ii) a plurality of zymogenes wherein for each target being detected, there exists at least one zymogene which encodes, but which itself is the anti-sense sequence of, a catalytic nucleic acid molecule having distinctly measurable activity, the primer and zymogene being situated with respect to each other so that, when the corresponding target is present, a single amplified nucleic acid molecule is produced which comprises the sequences of both the target and corresponding catalytic nucleic acid molecule; and
(b) simultaneously determining the presence of each of the catalytic nucleic acid activities, thereby determining the presence of each of the corresponding target nucleic acid sequences in the sample.

This invention further provides a DNA molecule comprising a primer and a zymogene, wherein the primer is situated 3' of the zymogene.

This invention still further provides a kit for use in determining the presence of a target nucleic acid sequence in a sample, which comprises
(a) a primer suitable for initiating amplification of the target;
(b) a zymogene which encodes, but which itself is the anti-sense sequence of, a catalytic nucleic acid sequence, wherein the primer and zymogene are situated with respect to each other so that, when the target is present, a single amplified nucleic acid molecule is produced which comprises the sequences of both the target and catalytic nucleic acid molecule; and
(c) reagents permitting primer-initiated nucleic acid amplification and catalytic nucleic acid activity.

Finally, this invention provides a kit for use in determining the presence of a plurality of target nucleic acid sequences in a sample, which comprises
(a) a plurality of primers, wherein for each target being detected, there exists at least one primer suitable for initiating amplification of that target;
(b) a plurality of zymogenes wherein for each target being detected, there exists at least one zymogene which encodes, but which itself is the anti-sense sequence of, a catalytic nucleic acid sequence having distinctly measurable activity, wherein the primer and zymogene are situated with respect to each other so that, when the corresponding target is present, a single amplified nucleic acid molecule is produced which comprises the sequences of both the target and corresponding catalytic nucleic acid molecule; and
(c) reagents permitting primer-initiated nucleic acid amplification and catalytic nucleic acid activity.

DETAILED DESCRIPTION OF THE INVENTION

Definitions

Figure 1:
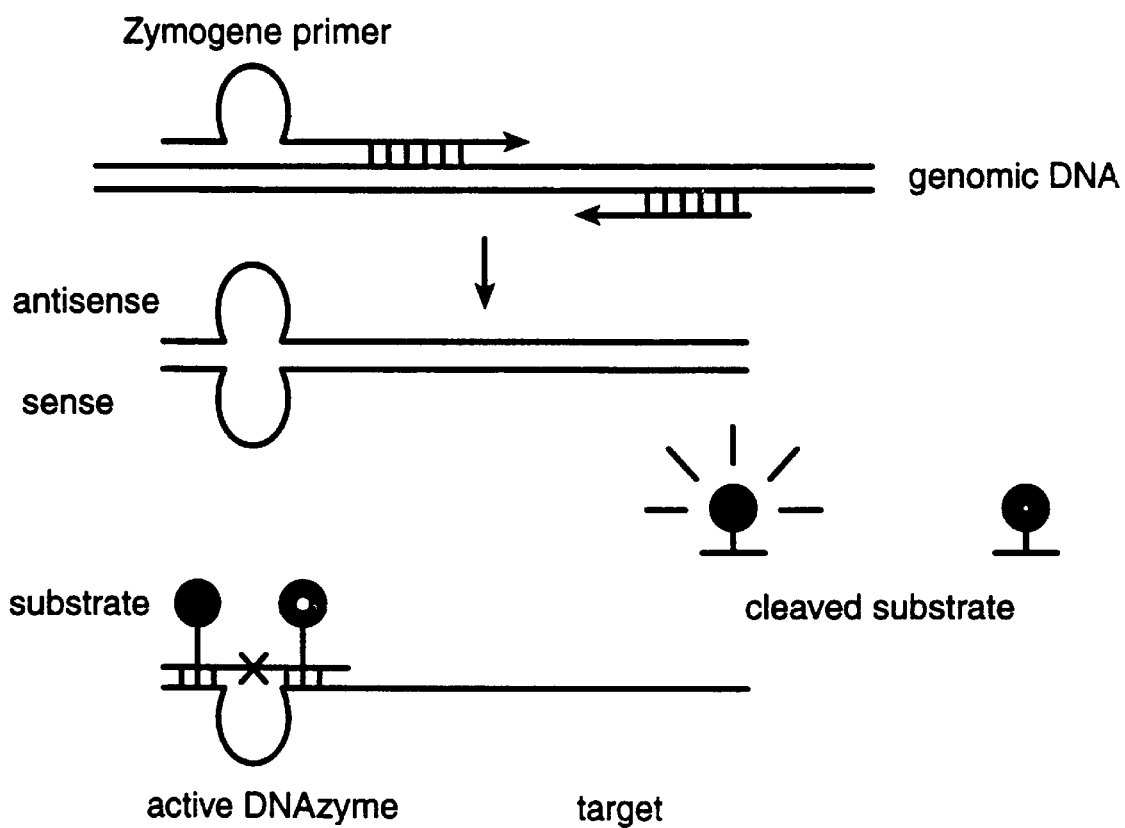
FIG. 1 shows a schematic of the instant method. Here, a nucleic acid molecule comprising a primer and zymogene is contacted with a segment of genomic DNA comprising a target sequence. This gives rise to a second nucleic acid molecule comprising a catalytic nucleic acid and a target. The catalytic nucleic acid in turn cleaves a detectable substrate.

In this invention, certain terms are used frequently which shall have the meanings set forth as follows. "Catalytic nucleic acid molecule", "catalytic nucleic acid", and "catalytic nucleic acid sequence" are equivalent, and each shall mean a DNA molecule or DNA-containing molecule (also known in the art as a "DNAzyme") or an RNA or RNA-containing molecule (also known in the art as a "ribozyme") which specifically recognizes a distinct substrate and catalyzes the chemical modification of this substrate. The nucleic acid bases in the DNAzymes and ribozymes can be the bases A, C, G, T and U, as well as derivatives thereof. Derivatives of these bases are well known in the art, and are exemplified in reference 40.

"Amplification" of a target nucleic acid sequence shall mean the exponential amplification thereof (as opposed to linear amplification), whereby each amplification cycle doubles the number of target amplicons present immediately preceding the cycle. Methods of exponential amplification include, but are not limited to, PCR, SDA and TMA. Exponential amplification differs from linear amplification, whereby in linear amplification, each amplification cycle increases by a fixed number the number of target amplicons present immediately preceding the cycle.

"Reporter substrate", "chemical substrate" and "substrate" are equivalent, and each shall mean any molecule which is specifically recognized and modified by a catalytic nucleic acid molecule. "Target" and "target nucleic acid sequence" are equivalent, and each shall mean the nucleic acid sequence of interest to be detected or measured by the instant invention, which comprises a sequence that hybridizes with the primer when contacted therewith in this method, and that can be either an entire molecule or a portion thereof. "Primer" shall mean a short segment of DNA or DNA-containing nucleic acid molecule, which (i) anneals under amplification conditions to a suitable portion of a DNA or RNA sequence to be amplified, and (ii) initiates, and is itself physically extended, via polymerase-mediated synthesis. Finally, "zymogene" shall mean a nucleic acid sequence which comprises the anti-sense (i.e. complementary) sequence of a catalytic nucleic acid molecule having detectable activity, and whose transcription product is the catalytic nucleic acid molecule.

Embodiments of the Invention

This invention provides a rapid and procedurally flexible method of detecting and quantitatively measuring target nucleic acid sequences of interest in a sample. This method is unique in that it simultaneously employs target amplification and detection via catalytic nucleic activity in a single reaction vessel. Moreover, it is unique in that the amplification product is a single nucleic acid molecule containing sequences for the target and the catalytic nucleic acid molecule. Finally, this method is the first to employ an anti-sense, zymogene sequence of a catalytic nucleic acid molecule which—only in the presence of the target sequence—is amplified in its "sense", catalytic form.

More specifically, this invention provides a method of detecting the presence of a target nucleic acid sequence in a sample which comprises
(a) contacting the sample, under conditions permitting primer-initiated nucleic acid amplification and catalytic nucleic acid activity, with
  (i) a DNA primer suitable for initiating amplification of the target, and
  (ii) a DNA zymogene which encodes, but which itself is the anti-sense sequence of, a catalytic nucleic acid molecule, wherein the primer and zymogene are situated with respect to each other so that, when the target is present, a single amplified nucleic acid molecule is produced which comprises the sequences of both the target and catalytic nucleic acid molecule; and (b) determining the presence of catalytic nucleic acid activity, thereby determining the presence of the target nucleic acid sequence in the sample.

In one embodiment, the instant method further comprises the step of quantitatively determining the amount of catalytic nucleic acid activity in the sample resulting from step (a), and comparing the amount of activity so determined to a known standard, thereby quantitatively determining the amount of the target nucleic acid sequence. The known standard can be any standard or control used for quantitative determination. Examples of these standards include (i) known reaction kinetic information, as well as (ii) signal measurements obtained using samples containing no catalytic activity, or a pre-determined amount of catalytic activity.

In one embodiment, the primer and zymogene are on separate DNA molecules, and the primer-initiated nucleic acid amplification is rolling circle amplification (a known amplification method). In a another embodiment, at least two of the DNA molecules comprise both the primer and zymogene.

In a further embodiment, the sample is contacted with two DNA molecules, each molecule comprising a primer, and at least one molecule comprising the zymogene wherein the primer is situated 3' of the zymogene.

In one form of this embodiment, the DNAzyme encoded by the zymogene recognizes and cleaves a sequence actually residing on the amplified nucleic acid molecule itself (i.e., cis cleavage, as opposed to trans cleavage whereby the DNAzyme cleaves a substrate located on a different molecule). More specifically, the single amplified nucleic acid molecule further comprises a nucleotide sequence recognized and cleaved in cis by the zymogene-encoded catalytic nucleic acid DNAzyme co-residing on the amplified molecule.

In the preferred embodiment of this method employing cis DNAzyme-catalyzed cleavage, the zymogene-encoded DNAzyme is a 10-23 DNAzyme, and the DNA primer used in step (a)(i) of the instant method (i.e., a "chimeric" primer) contains at least one purine ribonucleotide residue which serves as the 5' side of the site recognized and cleaved in cis by the 10-23 DNAzyme. This purine ribonucleotide residue in the chimeric primer is required for cleavage by the 10-23 DNAzyme. Thus, using this chimeric primer permits the 10-23 DNAzyme cleavage site to be generated in a PCR reaction. The chimeric primer can also include, for example, a ribonucleotide residue that serves as the 3' side of the site recognized and cleaved in cis by the 10-23 DNAzyme.

In this invention, the nucleic acid molecules comprising the primers and/or zymogenes can also comprise additional sequences, such as sequences complementary to the target.

The target sequence detected or quantitated in the instant methods can be any nucleic acid sequence. In one embodiment, the target nucleic acid sequence is a DNA molecule. In another embodiment, the target nucleic acid sequence is an RNA molecule, and step (a) further comprises the required step of first reverse transcribing the target RNA sequence to DNA prior to contacting the sample with the primer and zymogene.

The catalytic nucleic acid molecule encoded by the zymogene can be a ribozyme or a DNAzyme. In one embodiment, the catalytic nucleic acid molecule is a ribozyme. In another embodiment, the catalytic nucleic acid molecule is a DNAzyme.

The catalytic nucleic acid activity measured in the instant methods can be any activity which can occur (and, optionally, be measured) simultaneously and in the same milieu with a nucleic acid amplification reaction. The catalytic nucleic acid activity can comprise, for example, the modification of a detectable chemical substrate, which modification is selected from the group consisting of phosphodiester bond formation and cleavage, nucleic acid ligation and cleavage, porphyrin metallation, and formation of carbon-carbon, ester and amide bonds. In one embodiment, the detectable chemical substrate modification is cleavage of a fluorescently labeled nucleic acid molecule, preferably a DNA/RNA chimera.

In the preferred embodiment, the reporter substrate is cleaved, and measuring this cleavage is a means of measuring the catalytic activity. For example, the presence of the cleaved substrate can be monitored by phosphorimaging following gel electrophoresis provided the reporter substrate is radiolabelled. The presence of cleaved substrate can also be monitored by changes in fluorescence resulting from the separation of fluoro/quencher dye molecules incorporated into opposite sides of the cleavage site within the substrate. Such systems provide the opportunity for a homogeneous assay which can be monitored in real time. Methods for monitoring changes in fluorescence are well known in the art. Such methods include, by way of example, visual observation and monitoring with a spectrofluorometer.

The target nucleic acid sequence can be from any organism, and the sample can be any composition containing, or suspected to contain, nucleic acid molecules. In one embodiment, the target is from a plant, or from an animal such as, for example, a mouse, rat, dog, guinea pig, ferret, rabbit, and primate. In another embodiment, the target is in a sample obtained from a source such as water or soil. In a further embodiment, the target is from a sample containing bacteria, viruses or mycoplasma.

In the preferred embodiment, the target is from a human. The instant methods can be used for a variety of purposes including, for example, diagnostic, public health and forensic.

In one embodiment, the instant method is used for diagnostic purposes. Specifically, the invention can be used to diagnose a disorder in a subject characterized by the presence of at least one target nucleic acid sequence which is not present when such disorder is absent. Such disorders are well known in the art and include, by way of example, cancer, cystic fibrosis, and various hemoglobinopathies. The invention can also be used to diagnose disorders associated with the presence of infectious agents. Such disorders include, by way of example, AIDS, Hepatitis C, and tuberculosis. In the preferred embodiment, the subject being diagnosed is human and the disorder is cancer.

In another embodiment, the sample being tested for the presence or amount of target nucleic acid molecule is a sample taken for public health purposes. Examples of such samples include water, food and soil, possibly containing harmful pathogens such as bacteria, viruses and mycoplasma.

In a further embodiment, the sample being tested for the presence or amount of target nucleic acid molecules is a forensic sample. Examples of such samples include bodily fluids, tissues and cells, which can be obtained from any source such as a crime scene.

This invention also provides a method of simultaneously detecting the presence of a plurality of target nucleic acid sequences in a sample which comprises (a) contacting the sample, under conditions permitting primer-initiated nucleic acid amplification and catalytic nucleic acid activity, with
  (i) a plurality of primers wherein for each target being detected, there exists at least one primer suitable for initiating amplification of that target, and
  (ii) a plurality of zymogenes wherein for each target being detected, there exists at least one zymogene which encodes, but which itself is the anti-sense sequence of, a catalytic nucleic acid molecule having distinctly measurable activity, the primer and zymogene being situated with respect to each other so that, when the corresponding target is present, a single amplified nucleic acid molecule is produced which comprises the sequences of both the target and corresponding catalytic nucleic acid molecule; and
(b) simultaneously determining the presence of each of the catalytic nucleic acid activities, thereby determining the presence of each of the corresponding target nucleic acid sequences in the sample.

In one embodiment, the method of simultaneously detecting the presence of a plurality of targets further comprising the step of quantitatively determining the amount of each catalytic nucleic acid activity in the sample resulting from step (a), and comparing the amount of each activity so determined to a known standard, thereby quantitatively determining the amount of each target nucleic acid sequence. Examples of multiple targets which can be simultaneously detected by the instant methods are disclosed in reference 39.

This invention further provides a DNA molecule comprising a primer and a zymogene, wherein the primer is situated 3' of the zymogene. The instant molecule can be used pursuant to the instant methods.

This invention still further provides a kit for use in determining the presence of a target nucleic acid sequence in a sample, which comprises
  (a) a primer suitable for initiating amplification of the target;
  (b) a zymogene which encodes, but which itself is the anti-sense sequence of, a catalytic nucleic acid sequence, wherein the primer and zymogene are situated with respect to each other so that, when the target is present, a single amplified nucleic acid molecule is produced which comprises the sequences of both the target and catalytic nucleic acid molecule; and
  (c) reagents permitting primer-initiated nucleic acid amplification and catalytic nucleic acid activity.

Finally, this invention provides a kit for use in determining the presence of a plurality of target nucleic acid sequences in a sample, which comprises
  (a) a plurality of primers, wherein for each target being detected, there exists at least one primer suitable for initiating amplification of that target;
  (b) a plurality of zymogenes wherein for each target being detected, there exists at least one zymogene which encodes, but which itself is the anti-sense sequence of, a catalytic nucleic acid sequence having distinctly measurable activity, wherein the primer and zymogene are situated with respect to each other so that, when the corresponding target is present, a single amplified nucleic acid molecule is produced which comprises the sequences of both the target and corresponding catalytic nucleic acid molecule; and
  (c) reagents permitting primer-initiated nucleic acid amplification and catalytic nucleic acid activity.

In one embodiment, the instant kit further comprises reagents useful for isolating a sample of nucleic acid molecules from a subject or sample. The components in the instant kit can either be obtained commercially or made according to well known methods in the art, as exemplified in the Experimental Details section below. In addition, the components of the instant kit can be in solution or lyophilized as appropriate. In one embodiment, the components are in the same compartment, and in another embodiment, the components are in separate compartments. In the preferred embodiment, the kit further comprises instructions for use.

In the instant methods and kits, the nucleic acid amplification can be performed according to any suitable method known in the art, and preferably according to one selected from the group consisting of PCR, SDA and TMA.

Numerous methods are relevant to this invention which are within routine skill in the art. These include: methods for isolating nucleic acid molecules, including, for example, phenol chloroform extraction, quick lysis and capture on columns (34–38); methods of detecting and quantitating nucleic acid molecules; methods of detecting and quantitating catalytic nucleic acid activity; methods of amplifying a nucleic acid sequence including, for example, PCR, SDA and TMA (also known as (SSR))(1–10, 41); methods of designing and making primers for amplifying a particular target sequence; and methods of determining whether a catalytic nucleic acid molecule cleaves an amplified nucleic acid segment including, by way of example, polyacrylamide gel electrophoresis and fluorescence resonance energy transfer (FRET) (25, 31).

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Detection of K-ras in Tumor Cell DNA

A. PCR Primers

Three PCR primers (5KID, 3K2Dz3 and 3K2) were synthesized by Oligos Etc., Inc. (Wilsonville, Oreg., USA). The 5' PCR primer (5KID) is complementary to the human K-ras gene. The 3' primer 3K2Dz3 is a zymogene PCR primer which contains (a) a 5' region containing the catalytically inactive antisense sequence complementary to an active DNAzyme and (b) a 3' region which is complementary to the human K-ras gene. During PCR amplification using 5KID and 3K2Dz3, the amplicons produced by extension of 5KID contain both K-ras sequences and catalytically active sense copies of a DNAzyme incorporated in their 3' regions. The active DNAzyme is designed to cleave an RNA/DNA reporter substrate (Sub 1). The primer 3K2 is a control primer which contains the same K-ras-specific sequences which are incorporated in 3K2Dz3. However this primer contains no zymogene sequence. The sequences of the PCR primers are listed below. Sequences underlined are complementary to the human K-ras gene and the sequence in bold is the inactive (antisense) sequence which is complementary to an active DNAzyme.

5KID(SEQ ID NO:1) (5' K-ras primer)
GGCCTGCTGAAAATGACTGAATA
3K2Dz3(SEQ ID NO:2) (3' K-ras zymogene primer)
GAGAACTGCAATTCGTTGTAGCTAGC-
CTTTCAGGACCCA
CGTCCACAAAATGATTCTGA 3K2(SEQ ID NO:3) (3' K-ras primer for control reaction)

CGTCCACAAAATGATTCTGA

B. Reporter Substrate

The reporter substrate (Sub 1) was synthesized by Oligos Etc., Inc. (Wilsonville, Oreg., USA). Sub 1 is a chimeric molecule containing both RNA (bold, underlined) and DNA bases. It has a 3' phosphate group which prevents its extension by DNA polymerase during PCR. Sub 1 was 5' end-labeled with $^{32}$P by standard techniques (34). The sequence of Sub 1 is illustrated below.

Sub 1(SEQ ID NO:4)

GAGAACTGCAAUGUUTCAGGACCCA

C. DNAzyme for a Control Cleavage Reaction

The DNAzyme Dz3a was synthesized by Oligos Etc., Inc. (Wilsonville, Oreg., USA). This DNAzyme is designed to cleave Sub 1 at the same sequence which is cleaved by the active DNAzyme generated during PCR amplification using the zymogene primer 3K2Dz3. The sequence of Dz3a is illustrated below.

Dz3a (SEQ ID NO:5)

TCCTGAAAGGCTAGCTACAACGAATTGCAGT

D. Preparation of Genomic DNA from a Tumor Cell Line

The human cell line K562 was obtained from the American Type Culture Collection (Rockville, Md.). K562 is a leukemic cell line which harbours a wild type K-ras sequence. Genomic DNA was prepared by cationic polymer extraction (38).

E. PCR Amplification of the K-ras Gene

Genomic DNA isolated from K562 was amplified by PCR. Reactions (A1 and A2) contained genomic DNA (500 ng), 50 pmole of 5KID, 1 pmole of 3K2Dz3, 50 fmole of $^{32}$P-labeled Sub 1, each dNTP (dATP, dCTP, dTTP, dGTP) at 100 uM in 100 mM NaCl, 50 mM Tris (pH 8.3 at 25° C.) and 8 mM MgCl$_2$. Six units of Taq DNA polymerase (5 units/ul; AmpliTaq, Perkin Elmer) were mixed with 2 ul of TaqStart™ antibody (1.1 mg/ml, Clontech) in 1.8 ul of antibody dilution buffer (Clontech). The Taq DNA polymerase:TaqStart™ antibody mixture was incubated for 15 minutes at room temperature prior to addition to the PCR mixture. The total reaction volumes were 50 ul. One negative control reaction (B) contained all reaction components with the exception of genomic DNA. A second negative control reaction (C) contained all reaction components with the exception of 3K2Dz3 which was replaced with 1 pmole of 3K2. A positive control cleavage reaction (D) contained 30 pmole of Dz3a plus all reaction components present in control reaction C. The reactions were placed in a GeneAmp PCR system 9600 (Perkin Elmer), denatured at 94° C. for 2 minutes and then subjected to 20 cycles of 92° C. for 20 seconds and 58° C. for 30 seconds, followed by 20 cycles of 92° C. for 20 seconds, 74° C. for 1 second and 40° C. for 20 seconds.

F. Detection of Cleaved Reporter Substrate Sub 1

A 3 ul aliquot of each reaction was analyzed without subsequent manipulation by electrophoresis on a 16% denaturing polyacrylamide gel. The gel was visualized by phosphorimagery on a PhosphoImager: 445 S1 (Molecular Dynamics). The radiolabelled 25-base Sub 1 reporter substrate was cleaved to produce a radiolabelled fragment of 13 bases in the positive control cleavage reaction D. The same 13-base fragment was present in the PCR reactions A1 and A2 which contained both genomic DNA and the zymogene primer 3K2Dz3, indicating successful amplification of the K-ras gene by PCR. In the negative control reaction B (which contained no genomic DNA), only the 25-base fragment was evident, indicating cleavage of the substrate does not occur in the absence of amplification of target DNA. Finally, in the negative control reaction C, where the zymogene primer was replaced with a primer containing only K-ras sequences, the substrate was not cleaved since active DNAzymes are not produced in this reaction.

Example 2

Cleavage of a Fluorescent Reporter Substrate

A. Reporter Substrate

The reporter substrate, SubCz2, was synthesized by Oligos Etc., Inc. (Wilsonville, Oreg., USA). The sequence of SubCz2 is illustrated below. SubCz2 is a chimeric molecule containing both RNA (shown below in lower case) and DNA nucleotides. It has a 3' phosphate group that prevents its extension by DNA polymerase during PCR. SubCz2 was synthesized with a 6-carboxyfluorescein ("6-FAM") moiety attached to the 5' nucleotide (bold, underlined) and an N,N,N',N'-tetramethyl-6-carboxyrhodamine ("TAMRA") moiety attached to the first "T" deoxyribonucleotide (bold, underlined) 3' to the RNA bases. The cleavage of the reporter substrate can be monitored at 530 nm (FAM emission wavelength) with excitation at 485 nm (FAM excitation wavelength).

SubCz2(SEQ ID NO:6)

5' CCACTCguATTAGCTGTATCGTCAAGCCACTC 3'

B. PCR Primers

Two PCR primers were synthesised by Bresatec Pty. Ltd. (Adelaide, SA, Australia) or Pacific Oligos Pty. Ltd. (Lismore, NSW, Australia). The 5' PCR primer (5K49) is complementary to the human K-ras gene. The 3' primer (3K45Zc2) is a zymogene PCR primer which contains (a) a 5' region containing the catalytically inactive antisense sequence of an active DNAzyme and (b) a 3' region which is complementary to the human K-ras gene. During PCR amplification using 5K49 and 3K45Zc2, the amplicons produced by extension of 5K49 contain both K-ras sequences and catalytically active sense copies of a DNAzyme incorporated in their 3' regions. The active DNAzyme is designed to cleave the RNA/DNA reporter substrate SubCz2. The sequences of the PCR primers are illustrated below. The underlined portion of the sequence is complementary to the human K-ras gene, and the sequence shown in bold is the inactive (antisense) sequence that is complementary to the active DNAzyme.

5K49(SEQ ID NO:7) (5' K-ras primer)

5' CCTGCTGAAAATGACTGAATATAAA 3'

3K45Zc2(SEQ ID NO:8) (3' K-ras zymogene primer)

5' CCACTCTCGTTGTAGCTAGCCT ATTAGCTGTATCGTCAAGCCACTCTTGC 3'

C. Preparation of Genomic DNA from a Tumor Cell Line

The human cell line K562 was obtained from the American Type Culture Collection (Rockville, Md.). K562 is a leukemic cell line that harbours a wild type K-ras sequence. Genomic DNA was prepared by cationic polymer extraction (38).

D. PCR Amplification of the K-ras Gene

Genomic DNA isolated from K562 was amplified by PCR. Reactions contained 20 pmole 5K49, 3 pmole 3K45Zc2, 10 pmol SubCz2, 8 mM MgCl$_2$, 100 uM of each of dATP, dCTP, dTTP, and dGTP, and 1×buffer (75 mM KCl with 10 mM Tris pH 8.3 at 25° C.). All solutions used in the PCR were made up in DEPC-treated water. Three units of Taq DNA polymerase (5 units/ul AmpliTaq, Perkin-Elmer) were mixed with TaqStart™ antibody (Clontech) to give a final molar ratio of Taq DNA polymerase:TaqStart™ antibody of 1:10. The Taq DNA polymerase:TaqStart™ antibody mixture was incubated for 15 minutes at room temperature prior to addition to the PCR mixture. The total reaction volumes were made up to 50 ul. Duplicate reactions were set up which contained 500 ng of K562 genomic DNA. Control reactions contained all reaction components with the exception of genomic DNA. The reactions were placed in an ABI Prism 7700 Sequence Detection System and incubated at 40° C. for 1 minute (to provide a base line reading), denatured at 94° C. for 3 minutes, subjected to 20 cycles of 70° C. for 1 minute with a temperature decrease of 1° C. per cycle, and followed by incubation at 94° C. for 5 seconds. This was followed by a further 50 cycles at 40° C. for 1 minute, followed by incubation at 94° C. for 5 seconds.

Fluorescence was measured by the ABI Prism 7700 Sequence Detection System during the annealing/extension phase of the PCR. Reactions with genomic DNA showed an increase in FAM fluorescence at 530 nm over the fluorescence observed in control reactions. This fluorescence increase was used to monitor the accumulation of K-ras amplicons during PCR. These results confirm that zymogene PCR can be used to facilitate homogeneous amplification and real time detection in a simple fluorescent format.

Example 3

Use of Zymogenes to Distinguish Between Variant Alleles: Detection of Mutations at K-ras Codon 12

A. Strategy

PCR using zymogene primers can also be used for the analysis of point mutations. In this example, the zymogene primers facilitate synthesis of active DNAzymes during PCR. These DNAzymes are designed to cleave the PCR amplicons in cis only when their hybridizing arms are fully complementary to position 1 of codon 12 within K-ras. Walder, et al. (41) have previously shown that Taq DNA polymerase can extend DNA/RNA chimeric primers that contain one or two 3' terminal ribose residues. These chimeric primers are used here to produce PCR amplicons that serve as substrates for the 10-23 DNAzyme.

PCR using a 5' DNA/RNA chimeric primer (5K42r) and a 3' zymogene primer (3K42Dz2) amplified a region of K-ras. 5K42r hybridized to the K-ras sequence adjacent to codon 12 and contained the purine:pyrimidine residues which form the potential DNAzyme cleavage site. The zymogene primer 3K42Dz2 has a 3' region that is complementary to K-ras, and a 5' region that contains the antisense of a DNAzyme. The zymogene primer had no inherent catalytic activity itself but, when used in conjunction with 5K42r, it facilitated the production of amplicons having (a) DNAzyme cleavage sites near their 5' termini and (b) active (sense) DNAzymes at their 3' termini. This DNAzyme is designed to cleave the 5' end of the amplicons in cis. The 5' arm of the DNAzyme is fully complementary to sequences that are wild type at codon 12. Mutations at K-ras codon 12, which result in mismatches with the 5' DNAzyme arm, are predicted to significantly decrease the efficiency of DNAzyme cleavage.

B. Primer Sequences

5' chimeric primer 5K42r (SEQ ID NO:9)

(upper case—deoxyribonucleotide residues; lower case ribonucleotide residues)

5' TATAAACTTGTGGTAGTTGGAgcT 3'

3' zymogene primer 3K42Dz2(SEQ ID NO:10)

(complement of 10:23 catalytic core in bold)

5' ACTTGTGGTAGTTGGATCGTTG-TAGCTAGCCCTGG

TGGCAGCTGTATCGTCAAGGCACTC 3'

The primers were synthesised by Pacific Oligos Pty. Ltd. (Lismore, NSW, Australia) or Oligos Etc., Inc. (Wilsonville, Oreg., USA). The 5' primer, 5K42r, was 5' end-labelled with g-$^{32}$P by incubating 25 ul of 20 uM primer with 2.5 ul of polynucleotide kinase (10×10$^3$ U/ml, 3' phosphatase-free, Boehringer Mannheim), 2.5 ul rRNasin (40 U/ul recombinant rRNasin®, ribonuclease inhibitor, Promega), 5 ul of polynucleotide kinase buffer (Boehringer Mannheim), 10 ul of g-$^{32}$P Adenosine 5'-triphosphate (2.5 uM, Stable Label Gold™, Bresatec) and 5 ul of DEPC water for 30 minutes at 37° C.

C. K-ras DNA Templates pUC 18 plasmid vectors containing K-ras exon 1 sequences, which were either wild type (GGT) or mutated at codon 12 (CGT or AGT), were used as DNA templates for PCR.

D. Amplification by Zymogene PCR and Cleavage by DNAzymes Synthesised During the Reaction PCR mixtures contained 0.2 pg/ul K-ras plasmid DNA, 10 pmole of g-$^{32}$P-labelled 5K42r, 2 pmole 3K42Dz2, 1 mM DTT, 8 mM MgCl$_2$, each dNTP (dATP, dCTP, dTTP, dGTP) at 100 uM, 0.4 U/ul rRNasin®, and 1×buffer (100 mM NaCl with 50 mM Tris pH 8.3 at 25° C.). Duplicate reactions were set up for each DNA template. Six units of Taq DNA polymerase (5 units/ul AmpliTaq, Perkin-Elmer) were mixed with TaqStart™ antibody (Clontech) to give a final molar ratio of Taq DNA polymerase: TaqStart™ antibody of 1:5. The Taq DNA polymerase: TaqStart™ antibody mixture was incubated for 15 minutes at room temperature prior to addition to the PCR mix. The total reaction volumes were 50 ul. The reactions were placed in a GeneAmp PCR 9600 (Perkin-Elmer), denatured at 94° C. for 2 minutes, subjected to 30 cycles at 60° C. for 1 minute, followed by treatment at 94° C. for 20 seconds. The reaction was further subjected to 10 cycles at 50° C. for 1 minute, followed by treatment at 94° C. for 20 seconds.

A 2.5 ul aliquot of each reaction was mixed with 2.5 ul of loading dye (97.5% formamide, 0.1% xylene cyanol, 0.1% bromopheol blue and 0.01 M EDTA), incubated at 75° C. for 2 minutes, and then loaded immediately onto a pre-warmed 16% denaturing (urea) acrylamide gel. The gels were electrophoresed for approximately 1 hour. The PCR product and cleavage fragments were visualised by scanning the gel using a Molecular Dynamics Phosphorimager 445 S1.

Several bands were visible on the gel (data not shown). The fragments, in order of mobility from the slowest to the fastest (i.e., from the origin to the bottom of the gel) were (a) PCR amplicons (running as a doublet), (b) unincorporated primer and (c) cleaved PCR amplicons. Small amounts of two fragments, produced by background hydrolysis at the ribonucleotide residues within the 5'primer, were also visible running between the primer and cleaved amplicons and running parallel with the cleaved amplicons. In all reactions, PCR product and unincorporated primer were visible. Reactions containing template DNA that was wild type at codon 12 (i.e., those that were fully complementary to the DNAzyme) contained cleaved amplicons. Reactions containing template DNA that was mutated at codon 12 (i.e., those that were mismatched with the DNAzyme) did not contain cleaved amplicons. Only low levels of background hydrolysis products were visible at this position on the gel in these reactions.

The sequence below is an amplicon that is wild type at position 1 of codon 12 (underlined) shown in a conformation wherein the DNAzyme (bold) is hybridising in cis(SEQ ID NO.11).

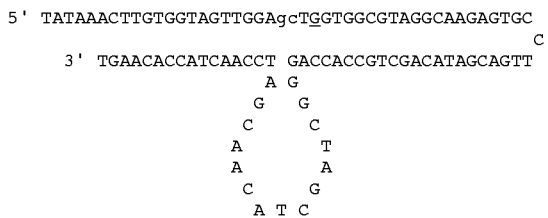

Based on this invention, and using routine methods of primer design, zymogene primers resulting in the production of DNAzymes can be readily designed which specifically cleave mutant K-ras sequences.

References
1. U.S. Pat. No. 4,683,202.
2. U.S. Pat. No. 4,683,195.
3. U.S. Pat. No. 4,000,159.
4. U.S. Pat. No. 4,965,188.
5. U.S. Pat. No. 5,176,995.
6. F. F. Chehab, et al. (1987) *Nature* 329:293–294.
7. R. K. Saiki, et al. (1985) *Science* 230:1350–1354.
8. Walker, G. T., et al. (1992) Strand Displacement Amplification—an isothermal, in vitro DNA amplification technique. *Nucleic Acids Res.* 20:1691.
9. Jonas, V., et al. (1993) Detection and identification of *Mycobacterium tuberculosis* directly from sputum sediments by amplification of rRNA. *Journal of Clinical Microbiology* 31:2410–2416.
10. Fahy, E., et al. (1991) Self-sustained sequence replication (3SR): An iso-thermal transcription-based amplification alternative to PCR. *PCR Methods Appl* 1: 25–33.
11. Nazarenko, I. A., et al. (1997) A closed tube format for amplification and detection of DNA based on energy transfer. *Nucleic Acids Research* 25: 2516–2521.
12. Tyagi, S. and Kramer, F. R. (1996) Molecular Beacons: Probes that fluoresce on hybridization. *Nature Biotechnology* 14: 303–308.
13. Lee, L. G., Connell, C. R. and Bloch, W. (1993) Allelic discrimination by nick-translation PCR with fluorogenic probes. *Nucleic Acids Research* 21:3761–3766.
14. Urdea, M. (1993) Synthesis and characterization of branched DNA (bDNA) for direct and quantitative detection of CMV, HBV, HCV and HIV. *Clin. Chem.* 39:725–726.
15. Eigen, M. and Rigler, R. (1994) Sorting single molecules: Application to diagnostics and evolutionary biotechnology. *PNAS* 91:5740–5747.
16. Perriman, R. and Gerlach, W. L. (1992) Extended target site specificity for a hammerhead ribozyme. *Gene* 113:157–163.
17. Breaker, R. R. and Joyce, G. (1994) A DNA enzyme that cleaves RNA. *Chemistry and Biology* 1:223–229.
18. Koizumi, M., et al. (1989) Design of RNA enzymes distinguishing a single base mutation in RNA. *Nucleic Acids Research* 17:7059–7069.
19. E. Otsuka and M. Koizumi, Japanese Patent No. 4,235,919.
20. Kashani-Sabet, M., et al. (1992) Reversal of the malignant phenotype by an anti-ras ribozyme. *Antisense Research and Development* 2:3–15.
21. Raillard, S. A. and Joyce, G. F. (1996) Targeting sites within HIV-1 cDNA with a DNA cleaving ribozyme. *Biochemistry* 35:11693–11701.
22. Carmi, N., et al. (1996) In vitro selection of self-cleaving DNAs. *Chemistry and Biology* 3:1039–1046.
23. Komatsu, Y., Koizumi, M., Sekiguchi, A. and Ohtsuka, E. (1993) Cross-ligation and exchange reactions catalyzed by hairpin ribozymes. *Nucleic Acid Research* 21:185–190.
24. Santoro, S. W. and Joyce, G. (1997) A general purpose RNA-cleaving DNA enzyme. *PNAS* 94:4262–4266.
25. Cuenoud, B. and Szostak, J. W. (1995) A DNA metalloenzyme with DNA ligase activity. *Nature* 375:611–614.
26. Li, Y. and Sen, D. A. (1996) A catalytic DNA for porphorin metallation. *Nature Struct. Biol.* 3:734–747.
27. Tarasow, T. M., Tarasow, S. L. and Eaton, B. E. (1997) RNA-catalyzed carbon-carbon bond formation. *Nature* 389: 54–57.
28. Illangasekare, M., Sanchez, Nickles, T., and Yarus, M. (1995) Aminoacyl-RNA synthesis catalyzed by an RNA. *Science* 267:643–647.
29. Lohse, P. A. and Szostak, J. W. (1996) Ribozyme-catalyzed amino-acid transfer reactions. *Nature* 381: 442–444.
30. Breaker, R. R. DNA enzymes (1997) *Nature Biotechnology* 15: 427431.
31. PCT International Publication No. WO 94/29481.
32. PCT International Publication No. WO 96/17087.
33. PCT International Publication No. WO 96/27026.
34. *Promega Protocols and Applications Guide.* Titus, D. E. (Ed) Promega Corporation (1991).
35. Kramvis, A., Bukofzer, S. and Kew (1996) Comparison of Hepatitis B virus DNA extractions from serum by the QIAamp blood kit, Genereleaser, and the Phenol-chloroform method. *Journal of Clinical Microbiology* 34: 2731–2733.
36. Yong, S. L., Thomas, R. J. S. and Phillips, W. A. (1995) Single-step direct PCR amplification from solid tissues. *Nucleic Acids Research* 23:1640.
37. Sambrook, J., Fritsch, E. F. and Maniatis, T. (1989) *Molecular Cloning: A Laboratory Manual.* 2nd Ed., New York: Cold Spring Harbour Laboratory Press.
38. U.S. Pat. No. 5,582,988.
39. PCT International Publication No. WO 96/32500.
40. PCR Systems, Reagents and Consumables. Perkin Elmer Catalogue 1996–1997. Roche Molecular Systems, Inc., Branchburg, N.J., USA.
41. Walder, R. Y., Hayes, J. R. and Walder J. A. (1993) Use of PCR primers containing a 3'-terminal ribose residue to prevent cross-contamination of amplified sequences. Nucleic Acid Research 21(18):4339–4343.

What is claimed is:

1. A method of detecting the presence of a target nucleic acid sequence in a sample which comprises
   (a) contacting the sample, under conditions permitting primer-initiated nucleic acid amplification and catalytic nucleic acid activity, with
      (i) a DNA primer suitable for initiating amplification of the target, and
      (ii) a DNA zymogene which encodes, but which itself is the anti-sense sequence of, a catalytic nucleic acid molecule, wherein the primer and zymogene are situated with respect to each other so that, when the target is present, a single amplified nucleic acid molecule is produced which comprises the sequences of both the target and catalytic nucleic acid molecule; and
   (b) determining the presence of catalytic nucleic acid activity, thereby determining the presence of the target nucleic acid sequence in the sample.

2. The method of claim 1, further comprising the step of quantitatively determining the amount of catalytic nucleic acid activity in the sample resulting from step (a), and comparing the amount of activity so determined to a known standard, thereby quantitatively determining the amount of the target nucleic acid sequence.

3. The method of claim 1, wherein the primer and zymogene are on separate DNA molecules, and the primer-initiated nucleic acid amplification is rolling circle amplification.

4. The method of claim 1, wherein the sample is contacted with two DNA molecules, each molecule comprising a primer, and at least one molecule comprising the zymogene wherein the primer is situated 3' of the zymogene.

5. The method of claim 4, wherein the single amplified nucleic acid molecule produced in step (a)(ii) further comprises a nucleotide sequence recognized and cleaved in cis by the zymogene-encoded catalytic nucleic acid co-residing on the amplified molecule.

6. The method of claim 5, wherein the zymogene-encoded catalytic nucleic acid is a 10-23 DNAzyme, and wherein the DNA primer of step (a)(i) contains at least one purine ribonucleotide residue which serves as the 5' side of the site recognized and cleaved in cis by the 10-23 DNAzyme.

7. The method of claim 4, wherein at least two of the DNA molecules comprise both the primer and zymogene.

8. The method of claim 1, wherein the target nucleic acid sequence is a DNA molecule.

9. The method of claim 1, wherein the target nucleic acid sequence is an RNA molecule, and step (a) further comprises the step of reverse transcribing the target nucleic acid sequence, if present, to DNA prior to contacting the sample with the primer and zymogene.

10. The method of claim 1, wherein the catalytic nucleic acid molecule is a ribozyme.

11. The method of claim 1, wherein the catalytic nucleic acid molecule is a DNAzyme.

12. The method of claim 1, wherein catalytic nucleic acid activity comprises the modification of a detectable chemical substrate, which modification is selected from the group consisting of phosphodiester bond formation and cleavage, nucleic acid ligation and cleavage, porphyrin metallation, and formation of carbon-carbon, ester and amide bonds.

13. The method of claim 12, wherein the detectable chemical substrate modification is cleavage of a fluorescently labeled nucleic acid molecule.

14. The method of claim 13, wherein the fluorescently labeled nucleic acid molecule is a DNA/RNA chimera.

15. The method of claim 1, wherein the target nucleic acid sequence is from an organism selected from the group consisting of human, bacterium, mycoplasma and virus.

16. The method of claim 15, wherein the target nucleic acid sequence is from a human.

17. The method of claim 16, wherein the presence of the target nucleic acid sequence in the sample is indicative of a genetic disorder.

18. The method of claim 1, wherein the sample is a forensic sample.

19. A method of simultaneously detecting the presence of a plurality of target nucleic acid sequences in a sample which comprises
   (a) contacting the sample, under conditions permitting primer-initiated nucleic acid amplification and catalytic nucleic acid activity, with
      (i) a plurality of primers wherein for each target being detected, there exists at least one primer suitable for initiating amplification of that target, and
      (ii) a plurality of zymogenes wherein for each target being detected, there exists at least one zymogene which encodes, but which itself is the anti-sense sequence of, a catalytic nucleic acid molecule having distinctly measurable activity, the primer and zymogene being situated with respect to each other so that, when the corresponding target is present, a single amplified nucleic acid molecule is produced which comprises the sequences of both the target and corresponding catalytic nucleic acid molecule; and
   (b) simultaneously determining the presence of each of the catalytic nucleic acid activities, thereby determining the presence of each of the corresponding target nucleic acid sequences in the sample.

20. The method of claim 19, further comprising the step of quantitatively determining the amount of each catalytic nucleic acid activity in the sample resulting from step (a), and comparing the amount of each activity so determined to a known standard, thereby quantitatively determining the amount of each target nucleic acid sequence.

21. The method of claim 1 or 19, wherein the nucleic acid amplification is performed according to a method selected from the group consisting of PCR, SDA and TMA.

22. A kit for use in determining the presence of a target nucleic acid sequence in a sample, which comprises
   (a) a primer suitable for initiating amplification of the target;
   (b) a zymogene which encodes, but which itself is the anti-sense sequence of, a catalytic nucleic acid sequence, wherein the primer and zymogene are situated with respect to each other so that, when the target is present, a single amplified nucleic acid molecule is produced which comprises the sequences of both the target and catalytic nucleic acid molecule; and
   (c) reagents permitting primer-initiated nucleic acid amplification and catalytic nucleic acid activity.

23. A kit for use in determining the presence of a plurality of target nucleic acid sequences in a sample, which comprises
   (a) a plurality of primers, wherein for each target being detected, there exists at least one primer suitable for initiating amplification of that target;
   (b) a plurality of zymogenes wherein for each target being detected, there exists at least one zymogene which encodes, but which itself is the anti-sense sequence of, a catalytic nucleic acid sequence having distinctly measurable activity, wherein the primer and zymogene are situated with respect to each other so that, when the corresponding target is present, a single amplified nucleic acid molecule is produced which comprises the sequences of both the target and corresponding catalytic nucleic acid molecule; and
   (c) reagents permitting primer-initiated nucleic acid amplification and catalytic nucleic acid activity.

24. The kit of claim 22 or 23, wherein the nucleic acid amplification is performed according to a method selected from the group consisting of PCR, SDA and TMA.

* * * * *

SEQUENCE LISTING

<160> NUMBER OF SEQ ID NOS: 11

<210> SEQ ID NO 1
<211> LENGTH: 23
<212> TYPE: DNA
<213> ORGANISM: Homo sapiens

<400> SEQUENCE: 1
ggcctgctga aaatgactga ata                                                    23

<210> SEQ ID NO 2
<211> LENGTH: 59
<212> TYPE: DNA
<213> ORGANISM: synthetic construct

<400> SEQUENCE: 2
gagaactgca attcgttgta gctagccttt caggacccac gtccacaaaa tgattctga             59

<210> SEQ ID NO 3
<211> LENGTH: 20
<212> TYPE: DNA
<213> ORGANISM: Homo sapiens

<400> SEQUENCE: 3
cgtccacaaa atgattctga                                                        20

<210> SEQ ID NO 4
<211> LENGTH: 23
<212> TYPE: RNA
<213> ORGANISM: synthetic construct

<400> SEQUENCE: 4
gagaacgcaa uguucaggac cca                                                    23

<210> SEQ ID NO 5
<211> LENGTH: 31
<212> TYPE: DNA
<213> ORGANISM: synthetic construct

<400> SEQUENCE: 5
tcctgaaagg ctagctacaa cgaattgcag t                                           31

<210> SEQ ID NO 6
<211> LENGTH: 31
<212> TYPE: DNA
<213> ORGANISM: synthetic construct

<400> SEQUENCE: 6
ccactcgatt agctgtatcg tcaagccact c                                           31

<210> SEQ ID NO 7
<211> LENGTH: 25
<212> TYPE: DNA
<213> ORGANISM: Homo sapiens

<400> SEQUENCE: 7
cctgctgaaa atgactgaat ataaa                                                  25

<210> SEQ ID NO 8
<211> LENGTH: 50
<212> TYPE: DNA
<213> ORGANISM: synthetic construct -continued

```
<400> SEQUENCE: 8
ccactctcgt tgtagctagc ctattagctg tatcgtcaag ccactcttgc            50

<210> SEQ ID NO 9
<211> LENGTH: 24
<212> TYPE: DNA
<213> ORGANISM: synthetic construct

<400> SEQUENCE: 9
tataaacttg tggtagttgg agct                                        24

<210> SEQ ID NO 10
<211> LENGTH: 60
<212> TYPE: DNA
<213> ORGANISM: synthetic construct

<400> SEQUENCE: 10
acttgtggta gttggatcgt tgtagctagc cctggtggca gctgtatcgt caaggcactc  60

<210> SEQ ID NO 11
<211> LENGTH: 98
<212> TYPE: DNA
<213> ORGANISM: synthetic construct
<220> FEATURE:
<223> OTHER INFORMATION: Description of Combined DNA/RNA Molecule:
      amplicon

<400> SEQUENCE: 11
tataaacttg tggtagttgg agctggtggc gtaggcaaga gtgccttgac gatacagctg  60
ccaccagggc tagctacaac gatccaacta ccacaagt                         98
```